US00PP09364P

United States Patent [19]

Zerr

[11] Patent Number: Plant 9,364

[45] Date of Patent: Nov. 7, 1995

[54] POINSETTIA PLANT NAMED 'FISCOR'

[75] Inventor: Katharina Zerr, Simmern, Germany

[73] Assignee: Florfis AG, Binningen, Switzerland

[21] Appl. No.: 327,928

[22] Filed: Oct. 24, 1994

[30] Foreign Application Priority Data

Feb. 9, 1994 [DE] Germany ..... EUP 156

[51] Int. Cl.[6] ..... A01H 5/00

[52] U.S. Cl. ..... Plt./86.4

[58] Field of Search ..... Plt./86.4

*Primary Examiner*—James R. Feyrer

*Attorney, Agent, or Firm*—Foley & Lardner

[57] ABSTRACT

A distinct cultivar of poinsettia plant named Fiscor, characterized by the combined traits of dark red bract color, good cyathia retention, medium and well branched plant habit, dark green foliage with weakly lobed leaves, and medium early flowering response.

1 Drawing Sheet

The present invention relates to a new and distinct cultivar of poinsettia plant, botanically known as *Euphorbia pulcherrima,* and referred to by the cultivar name Fiscor.

The new cultivar is a product of a planned breeding program carried out by the inventor Katharina Zerr in Hillscheid, Germany. The general objective of the breeding program was to create new cultivars having red bract coloration, dark green foliage, and good branching ability.

The new cultivar was originated from a hybridization made by the inventor in Hillscheid, Germany in 1992. The female parent was a hybrid seedling from unknown parentage and characterized by its orange-red bract color and medium green foliage. The male parent was the cultivar Lilo, disclosed in U.S. Plant Pat. No. 6,694 and characterized by its dark red bract color, dark green foliage, early flowering, but often inferior branching and plant habit.

Seeds from the cross germinated in November 1992, and in January 1993 a cutting was taken by the inventor from each seedling. The plants grown from these cuttings started flowering after short day treatment in May 1993, and Fiscor (Seedling No. 275) was selected from among these single stem plants.

Following final selection, additional cuttings were taken by the inventor from the original seedling No. 275 and these cuttings were grafted on rootstocks of the cultivar Peterstar to induce better branching ability. Peterstar is a commercial but unpatented cultivar characterized by its bright red bract color, medium green foliage, comparatively compact plant habit, medium early flowering response in autumn, and good branching ability.

The grafted plants were grown out and asexually propagated by or under the supervision of the inventor in Hillscheid, Germany by taking cuttings in the form of a stem with several leaves from the scion, for the purpose of building up mother stock and confirming the stability of the new cultivar. Horticultural examination initiated in autumn 1993 and continuing thereafter has demonstrated that the combination of characteristics as herein disclosed for Fiscor are firmly fixed and are retained through successive generations of asexual reproduction. The new cultivar has the excellent branching characteristics of Peterstar while retaining all other desirable characteristics of seedling No. 275.

The following traits have been repeatedly observed and are determined to be basic characteristics of Fiscor which in combination distinguish this poinsettia as a new and distinct cultivar:

1. Dark red flower color.
2. Good retention of cyathias.
3. Medium tall and well branched plant habit.

4. Dark green foliage with weakly lobed leaves.
5. Medium early flowering response.

Fiscor has not been observed under all possible environmental conditions. The phenotype may vary significantly with variations in environment such as temperature, light intensity, and daylength without, however, any variance in genotype. The following observations, measurements and comparisons describe plants grown in Hillscheid, Germany, under greenhouse conditions which approximate those generally used in commercial practice.

Of the many commercial cultivars known to the inventor, the most similar in comparison to Fiscor is the male parent Lilo. In general comparison to Lilo, Fiscor has a very similar flower color, similar dark green foliage, but broader plant habit and better branching ability. The flower response of Fiscor is later, but bracts are already colored 1–2 weeks before cyathias open. As a result, plants of Fiscor are saleable only one week later than Lilo, but stay marketable for a longer time because cyathias hold very well.

The accompanying color photographic drawing shows typical inflorescence and foliage of Fiscor, with colors being as true as possible with illustrations of this type. In the photograph, a typical mature potted plant of Fiscor appears on the left and a mature potted plant of comparison cultivar Lilo appears on the right.

In the following description, color references are made to the Royal Horticultural Society Colour Chart. The color values were determined indoors in a north light. The plants described were grown in Hillscheid, Germany (latitude 50°N). They were planted as rooted cuttings into 14 cm pots in early August, pinched in mid-August, and grown in the greenhouse under natural light conditions in late summer and autumn at 18° C. night temperature and 18° to 24° C. day temperature. Observations and measurements were taken at the beginning of flowering when 3 cyathias were open.

Classification:

*Botanical.*—*Euphorbia pulcherrima.*

*Commerical.*—Poinsettia, cv. Fiscor.

Parentage:

*Male parent.*—Lilo.

*Female parent.*—A hybrid seedling from unknown parentage, having orange-red flowers and medium green foliage. The resulting seedling No. 275 was grafted to the cultivar Peterstar to improve branching ability.

Plant description:

*Form.*—Broad, bushy, 8–10 branches.

*Growth habit.*—Medium height: 35–40 cm.

*Rooting.*—Medium: 20–24 days.

*Blooming season.*—From early December (about 9–10 weeks of response time).

*Blooming habit.*—Saleable in late November, when 3–6 bracts are colored.

*Foliage.*— Size: Leaf is approximately 14 cm in length; petiole is 8 cm in length. Internodes: 20–25 mm. Color: New Foliage: Upper surface, medium green, between 137A and 146A; under surface 146B. Old Foliage: Upper surface, dark green 139A; under surface 137A. Leaf Petiole: Dark red. Shape: Broad, elliptic with weak lobes, rounded base. Texture: Upper side, smooth; lower side, weak veins. Edge of margin: Entire. Disease resistance: None observed.

Flowering description:

*Cyathias.*— Borne: In a narrow cluster. Quantity: 18–23. Retention: Good.

*Bracts.*—Ovate or elliptical, some with weak lobes, smooth surface; largest colored bract with petiole is 18 cm long.

*Color.*—Dark red 46B.

*Aspect.*—Horizontal.

Reproductive organs:

*Glands, nectar cups.*—Yellow.

*Stamens.*—Dark red filament.

*Pollen.*—Plentiful, yellow in color.

*Styles.*—Dark red, 6-lobed stigma.

*Ovaries.*—Triangular, 3-celled, 3 ovules.

I claim:

1. A new and distinct poinsettia plant named Fiscor, as illustrated and described.

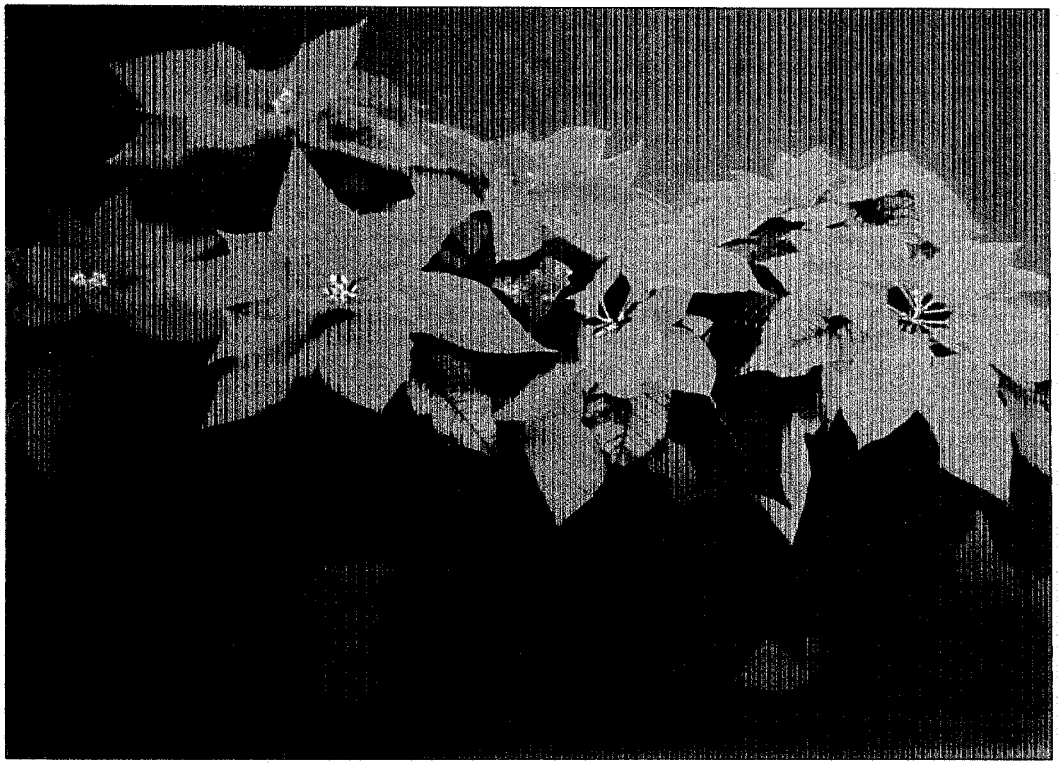

* * * * *